US007024234B2

(12) United States Patent
Margulies et al.

(10) Patent No.: US 7,024,234 B2
(45) Date of Patent: Apr. 4, 2006

(54) METHOD AND APPARATUS FOR MONITORING THE AUTONOMIC NERVOUS SYSTEM

(76) Inventors: Lyle Aaron Margulies, 5546 - 34th Ave. NE., Seattle, WA (US) 98105; David B. Harrell, 5122 - 103rd St. SW., Mukilteo, WA (US) 98275; Michael Riggins, 320 NE. 57th St., Seattle, WA (US) 98105

( * ) Notice: Subject to any disclaimer, the term of this patent is extended or adjusted under 35 U.S.C. 154(b) by 285 days.

(21) Appl. No.: 10/666,121

(22) Filed: Sep. 19, 2003

(65) Prior Publication Data

US 2004/0059236 A1    Mar. 25, 2004

Related U.S. Application Data

(60) Provisional application No. 60/412,310, filed on Sep. 20, 2002.

(51) Int. Cl.
*A61B 5/02* (2006.01)
(52) U.S. Cl. ...................... 600/324; 600/310
(58) Field of Classification Search ................ 600/324, 600/323, 310, 500, 501
See application file for complete search history.

(56) References Cited

U.S. PATENT DOCUMENTS

| | | | |
|---|---|---|---|
| 4,859,057 A * | 8/1989 | Taylor et al. ............... 600/473 |
| 5,299,188 A | 3/1994 | Hotta et al. ............. 364/413.05 |
| 5,520,176 A | 5/1996 | Cohen .......................... 128/630 |
| 5,605,151 A * | 2/1997 | Lynn ........................... 600/323 |
| 5,999,846 A | 12/1999 | Pardey et al. ................ 600/544 |
| 6,091,973 A | 7/2000 | Colla et al. .................. 600/324 |
| 6,228,033 B1 | 5/2001 | Koobi et al. ................. 600/483 |
| 6,272,378 B1 | 8/2001 | Baumgart-Schmitt ....... 600/544 |
| 6,319,205 B1 | 11/2001 | Goor et al. .................. 600/485 |
| 6,322,515 B1 | 11/2001 | Goor et al. .................. 600/485 |
| 6,358,201 B1 | 3/2002 | Childre et al. .............. 600/300 |
| 6,363,270 B1 | 3/2002 | Colla et al. ................. 600/324 |
| 6,402,698 B1 | 6/2002 | Mault ......................... 600/532 |

OTHER PUBLICATIONS

Meoli et al.; Hypopnea in Sleep-Disordered Breathing in Adults; SLEEP. vol. 24, No. 4, 2001; pp. 469-470.

(Continued)

*Primary Examiner*—Eric F. Winakur
*Assistant Examiner*—Vivek Natarajan
(74) *Attorney, Agent, or Firm*—Garrison & Associates PS; David L. Garrison (57) ABSTRACT

An apparatus and method for detection and monitoring of autonomic nervous system (ANS) activity in humans, primarily in the field of sleep research. The present invention discloses a portable, simple, and cost-effective electronic device containing hardware and software that permits real-time monitoring of a pulsatile blood volume waveform obtained through use of a photoplethysmographic (optical volume detecting) probe, thereby allowing signal conditioning, waveform slope analysis, display, recording, and output of pulse transitional slope data representative of activity in the ANS.

16 Claims, 7 Drawing Sheets

OTHER PUBLICATIONS

Pitson et al.; Value of beat-to-beat blood pressure changes, detected by pulse transit time, in the management of the obstructive sleep apnoea/hypopnoea syndrome; Eur Respir J ; 1998; 12: 685-692.

Bakewell; The Autonomic Nervous System; Update in Anasthesia; Issue 5; 1995; Article 6; pp. 1-2.

Pagani et al.; Detection of Central and Obstructive Sleep Apnea in Children Using Pulse Transit Time; International Symposium ISMDA-2002 Proceedings; Rome, Italy; Oct. 10-11, 2002; Berlin: Springer-Verlag; pp. 144-158.

* cited by examiner

FIG.1

LIGHT SOURCE

FINGER VASCULAR BED

PHOTODETECTOR

VARIABLE ABSORPTION DUE TO PULSE-ADDED VOLUME OF ARTERIAL BLOOD

ABSORPTION DUE TO ARTERIAL BLOOD

ABSORPTION DUE TO VENOUS BLOOD

ABSORPTION

ABSORPTION DUE TO TISSUE

TIME

METHOD AND APPARATUS FOR MONITORING THE AUTONOMIC NERVOUS SYSTEM

CROSS-REFERENCE TO RELATED APPLICATION

This application claims benefit of U.S. Provisional Application Ser. No. 60/412,310 entitled Method and Apparatus for Monitoring the Autonomous Nervous System, filed Sep. 20, 2002.

TECHNICAL FIELD

This invention relates to medical devices, and more particularly to physiological monitoring methods and devices used for detection of autonomic nervous system (ANS) activity in the field of sleep research. The present invention discloses a portable, simple, and cost-effective electronic sleep diagnostic device containing hardware and software that permits recording and signal conditioning of a pulsatile blood volume waveform obtained through use of a photoplethysmographic (optical volume detecting) probe, thereby allowing analysis pulse transitional slope data that is representative of activity in the autonomic nervous system (ANS).

BACKGROUND OF THE INVENTION

Cardiovascular risk is directly linked to sleep related breathing disorders (SRBD). The number of U.S. laboratories that study sleep, roughly 2,792, is incredibly low when compared to the number of Americans estimated to have a chronic SRBD, just over 40 million. The average number of beds per lab is 3.6 bringing the total number of beds in which to do a sleep study to roughly 10,000. This means that to test all 40 million Americans, there would be 4,000 patients that would be seen per bed. If sleep tests were run 365 days per year, the result is an astounding 11 years of conclusive tests needed to be run to test the current population of individuals suffering form SRBD. The length of time increases as one considers the actual number of days per year sleep labs actually test patients, plus the amount of tests that need to be re-run due to inconclusive testing, plus the number of patients that continually need to be retested to see if their treatment is functioning properly. Given this scenario, it is no shock that wait times for patients to be scheduled for a sleep test can typically range from six weeks to six months. The problem will only increase, as "it is estimated that nearly 80 million Americans will have a sleep problem by the year 2010 and 100 million will have one by the year 2050." Clearly then, the problem with wait time for testing should be addressed immediately to relieve pent up demand.

The current "gold standard" for testing sleep related breathing disorders is full polysomnography. Full polysomnography is, however, quite labor intensive, requires considerable instrumentation and is therefore rather expensive to conduct. As a result, many sleep laboratories have found it difficult to keep up with the demand for this test, and a long waiting list becomes the norm. Given that obstructive sleep apnea (OSA) is quite prevalent, leads to serious complications and that treatment options exist, it is important that individuals suffering from the disease are identified.

The need to study the ANS has been realized in academia for a considerable time. It is known in the field of microneurography that rapid-eye movement (REM) sleep is associated with profound sympathetic activity. It has also been found that arousals from non-rapid-eye movement (NREM) elicits K complexes that are associated with sympathetic activity. The sympathetic division of the ANS prepares a body for movement. Arousals require movement and hence an arousal requires sympathetic activation.

Generally, patients with OSA, a type of SRBD, have extremely disrupted sleep and terribly high daytime somnolence. Obstructive sleep apnea events are always accompanied by an acute rise in systolic blood pressure (rises in systolic blood pressure are associated with sympathetic activation), even when the usual EEG criteria for arousals are not met (a recognizable cortical electroencephalographic arousal). The duration of the apnea of individuals that demonstrate EEG arousal and those that do not meet the usual criteria for defining an arousal have been found to be identical. The pleural pressure peak, at the end of apnea, is identical between the two types of arousals, as are the EEG frequencies. These findings suggest that monitoring the cardiac changes of sleep is a more accurate measurement.

It has been demonstrated that apneic episodes result in progressive increases in sympathetic nerve activity. The increases are most marked toward the end of the apnea, when a patient moves. These findings are exactly what is excepted of sympathetic activation and its relationship to arousals in patients with SRBD.

Because cardiovascular control during sleep is primarily dictated by brain states that produce profound variation in ANS activity, many studies have been conducted to monitor the ANS. Since the data shows clearly that monitoring the ANS or cardiac changes in sleep yields more accurate data defining an arousal in sleep, it is clear that diagnostic studies must include ANS or cardiac monitoring.

It has been shown that in transitions from NREM to REM sleep, heart rate accelerations precede the EEG arousals marking the onset of REM. Therefore, not only does monitoring ANS activity give the clinician a possibly more accurate study, but also changes in ANS activity precede that information being observed via the EEG electrodes.

There are two existing technologies that attempt to monitor the ANS, namely pulse transit time (PTT) and peripheral arterial tonometry (PAT). Neither PTT nor PAT can lay claim to monitoring the ANS without adding additional sensors. PTT requires the use of ECG electrodes that may be difficult for a patient to self-apply due to skin cleaning and shaving requirements. PAT requires a very costly gauntlet-type device with a single-use finger pressure cuff. Also, the addition of extra sensors adds to noise artifact and difficulty in patient use. It is therefore an object of the present invention to provide an improvement over existing PTT and PAT technology through a more economical and more easily used device without need of additional sensors.

Several disclosures have been made in the prior art that teach methods and devices for diagnosis and monitoring of sleep breathing disorders using physiological data obtained from pulse oximetry-derived waveforms.

U.S. Pat. No. 5,398,682 to Lynn (Mar. 21, 1995) discloses a method and apparatus for the diagnosis of sleep apnea utilizing a single interface with a human body part. More specifically, a device is disclosed for diagnosing sleep apnea by identifying the desaturation and resaturation events in oxygen saturation of a patient's blood. The slope of the events is determined and compared against various information to determine sleep apnea.

U.S. Pat. No. 6,363,270 B1 to Colla, et al. (Mar. 26, 2002) discloses a method and apparatus for monitoring the occurrence of apneic and hypopneic arousals utilizing sensors placed on a patient to obtain signals representative of at least two physiological variables, including blood oxygen concentration, and providing a means for recording the occurrence of arousals. Obtained signals pass through conditioning circuitry and then processing circuitry, where correlation analysis is performed. A coincident change in at least two of the processed signals are indicative of the occurrence of an arousal that in turn indicates an apneic or hypopneic episode has occurred. A patient thus can be diagnosed as suffering conditions such as obstructive sleep apnea.

U.S. Pat. No. 6,529,752 B2 to Krausman and Allen (Mar. 4, 2003) discloses a method and apparatus for counting the number of sleep disordered breathing events experienced by a subject within a specified time period. Such a counter comprises: (1) an oxygen saturation level sensor for location at a prescribed site on the subject, (2) an oximetry conditioning and control module that controls the operation of the sensor and converts its output data to oxygen saturation level data, (3) a miniature monitoring unit having a microprocessor, a memory device, a timer for use in time-stamping data, a display means and a recall switch, and (4) firmware for the unit that directs: (i) the sampling and temporary storage of the oxygen saturation level data, (ii) the unit to analyze using a specified method the temporarily stored data to identify and count the occurrence of the subject's disordered breathing events, and to store the time of occurrence of each of these events, and (iii) the display means to display specified information pertaining to the counts in response to the actuation of the recall switch.

U.S. Pat. No. 6,580,944 B1 to Katz, et al. (Jun. 17, 2003) discloses a method and apparatus for identifying the timing of the onset of and duration of an event characteristic of sleep breathing disorder while a patient is awake. Chaotic processing techniques analyze data concerning a cardiorespiratory function, such as oxygen saturation and nasal air flow. Excursions of the resulting signal beyond a threshold provide markers for delivering the average repetition rate for such events that is useful in the diagnosis of obstructed sleep apnea and other respiratory dysfunctions.

The above references all make use of oxygen saturation data obtained through pulse oximetry to determine arousals and/or sleep breathing disorders. Each necessarily requires additional analysis and calculation of blood oxygen concentrations in order to render information useful specifically in the diagnosis and monitoring of sleep breathing disorders. It is therefore another object of the present invention to provide a more simplified method of obtaining and analyzing physiological data that accurately represents ANS activity.

BRIEF SUMMARY OF THE INVENTION

It is an object of the present invention to overcome one or more of the problems with the prior art. In one preferred embodiment the present invention provides a method and apparatus for improved monitoring of ANS activity using a single patient sensor.

A variety of breathing disturbances may occur during sleep, including snoring, hypoventilation, apnea, increased upper-airway resistance, and asthma related conditions. This project proposes development of a novel device that can noninvasively and accurately detect frequent brief micro arousals that are not well identified by conventional airflow, respiratory effort, pulse oximetry and EEG methods. These subcortical events result from increased respiratory effort and cause disruption of nocturnal sleep, leading to excessive daytime somnolence.

Since microarousals have been associated with changes in autonomic system outflow, this invention provides for a small, portable device that analyzes the shape of the arterial finger pulse, thereby detecting on a beat by beat basis changes in vascular tone directly attributable to microarousals. The present invention uses a photoplethysmographically derived arterial blood volume waveform for monitoring changes in peripheral arterial vascular tone, in conjunction with A/D converters and a microcontroller for analyzing the morphology of the pulsatile signal.

The method of the present invention provides for detection of microarousals that compares favorably with detection by pulse transit time (PTT) devices, EEG analysis, ECG analysis, esophagal pressure (Pes) or some combination of these methods. Although PTT and peripheral arterial tonometry (PAT) have both been receiving much attention as techniques for detecting changes in the ANS during sleep studies, PAT is relatively expensive and PTT has implementation problems caused by motion artifact.

It is a further object of the present invention to provide an apparatus that utilizes transmitted light intensity from an existing FDA approved pulse oximeter probe so that no additional device is attached to the patient. Valuable diagnostic information can then be extracted through electronic processing of this existing data.

Normalization is a method to correct for the photoplethysmographic pulse signal morphological changes based on finger position (as opposed to actual changes of autonomic activity.) PTT and PAT lack a means for signal normalization and therefor cannot correct for finger position changes. Normalization provides immunity to artifact caused by both elevation changes of the finger probe, and changes in blood flow due to arterial compression during patient positional changes. It is therefor another object of the present invention to provide a means of normalization in order to ensure appropriate artifact suppression.

Since pulse oximeters use an alternating flashing of two different wavelength LEDs, the present invention is intended to synchronize with the desired LED in order to examine the transmitted intensity due to a single wavelength. Alternatively, certain models of oximeter OEM modules provide an analog or digital output that can be utilized directly by the present invention.

Another objective is to provide algorithms for slope detection, peak to peak height, and normalization may be performed either with firmware within the present invention apparatus, or by software after the data is downloaded into a polysomnograph or other data processing device.

It is a further objective of the present invention to provide a means of data storage and transfer, and to provide a method of displaying the observed changes in slope. Alternative embodiments display these changes as a waveform, light bars, and/or numerical information.

DETAILED DESCRIPTION OF THE INVENTION

A variety of breathing disturbances may occur during sleep, including snoring, hypoventilation, apnea, increased upper-airway resistance, and asthma related conditions. The present invention discloses a method and apparatus that can noninvasively and accurately detect frequent brief "microarousals" (small amplitude subcortical disturbances that disrupt normal sleep) that are not well identified by conventional airflow, respiratory effort, pulse oximetry and EEG methods. These subcortical events result from increased respiratory effort and cause disruption of nocturnal sleep, leading to excessive daytime somnolence.

Microarousals can be detected using data obtained from the absorbance of visible or infrared light in a finger or other body part of a patient, and by analyzing changes in the obtained peripheral blood volume waveform that are indicative of microarousals. Specifically, sufficient information is contained in slope variations of the rising edge of the pulsatile blood volume waveform to allow analysis of changes in the autonomic nervous system (ANS). This technology is herein referred to as pulse transitional slope (PTS). Both ANS and hemodynamic responses occur during obstructive sleep apnea and are influenced by apnea, hypopnea, hypercapnea, and arousal.

Analysis of the noninvasive blood pressure pulse wave has been shown to be useful for evaluation of vascular load and aging. Pressure transducers located at a palpable artery, such as the carotid, femoral, or radial artery provided a detailed waveform of pressure versus time. This continuous pulse wave tracing contains precise waveshape, frequency, and inflection information easily discernable by the human eye that is not available from only systolic and diastolic pressure numerics. The progression from pressure transducers to photoplethysmography allows detection of the pulse wave at sites not easily palpated, including the finger and earlobe. Photoplethysmography detects the changes in the amount of light absorbed by hemoglobin, which corresponds to changes in blood volume. Changes in amplitude of the photoplethysmographic wave have been used to evaluate arterial compliance, but the wave contour itself was not used, as is disclosed by the present invention.

Figure 1:
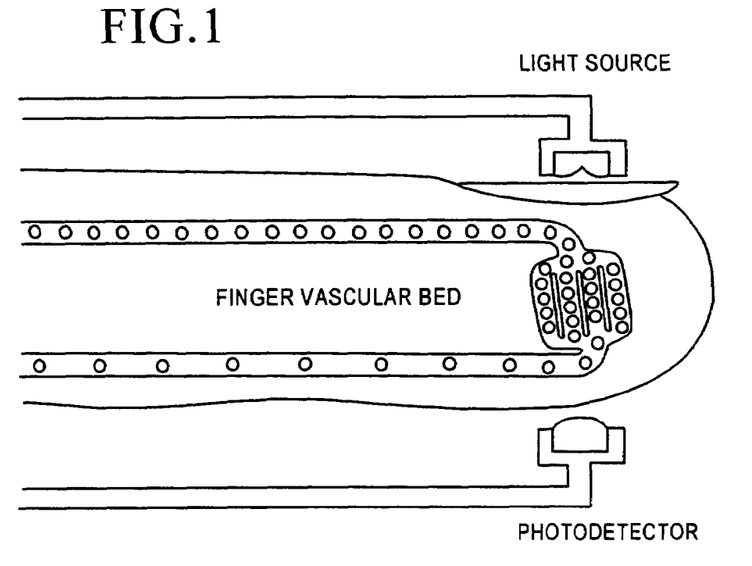
FIG. 1 shows a schematic representation of a typical pulse oximeter sensing configuration on a finger.

Plethysmography is the measurement of volume changes of tissue or an organ. Photoplethysmography measures blood volume changes in a tissue using the fractional change in light transmission. One of the most common applications of this technology is the noninvasive measurement of the oxygen saturation of the hemoglobin in red blood cells through a technique called pulse oximetry. FIG. 1 shows a typical pulse oximeter sensing configuration on a finger. Typically, two different wavelengths of light (e.g. 660 and 805 nm) are applied to one side of a finger and the received intensity is detected on the opposite side after experiencing some absorption by the intervening vascular tissues. The amount of absorption (and conversely transmission) is a function of the thickness, color, and structure of the skin, tissue, bone, blood, and other tissues that the light traverses.

The present invention is specifically directed to alpha andrenergic receptor sites, the activation of these receptors at certain locations on the body resulting in physiological responses such as peripheral vascular resistance, mydriasis, and contraction of pilomotor muscles, which are representative of sympathetic nervous system activity. The preferred locations generally include the fingers and the big toe (other sites are under investigation), due to a desirable lack of beta or parasympathetic receptors at those locations on the body.

The transmitting light comes from light emitting diodes (LEDs), typically in the visible red and the invisible infrared (IR) spectrums. The optical receiver may be a photodiode, photoresistor, or solar cell. By using two different wavelengths, each with different absorbance characteristics in oxygenated and deoxygenated blood, the intensity ratio between the two received signals can be analyzed, and not just the intensity. Therefore the attenuating tissues mentioned earlier do not affect the ratio of the intensities, which via a look-up table can determine the oxygen saturation percent in the finger vasculature.

Figure 2:
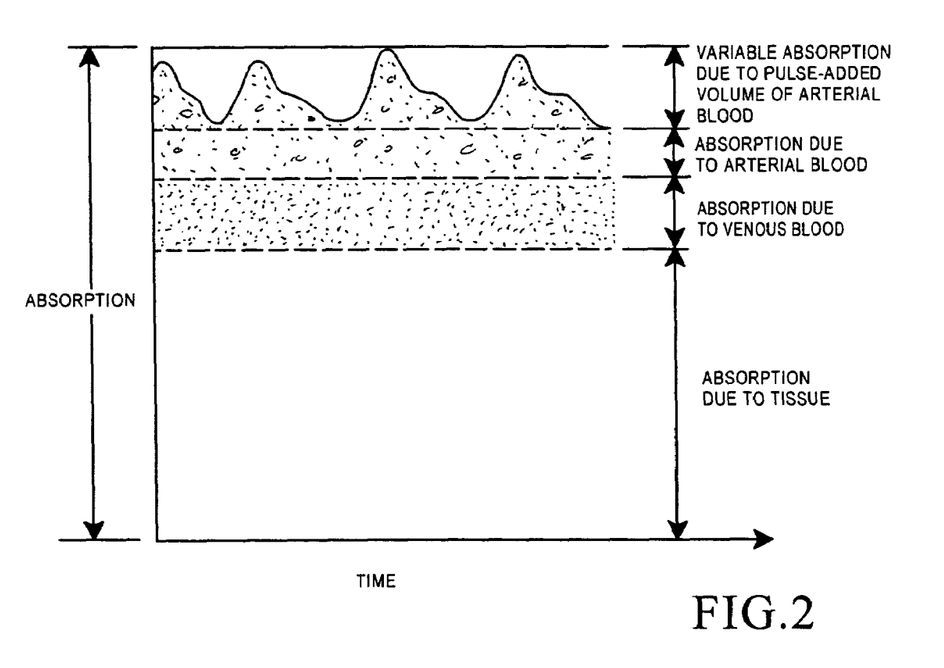
FIG. 2 shows a graphic representation of the components of vascular tissue that contribute to light absorption plotted as absorption versus time.

FIG. 2 shows the components of vasculature tissue that contribute to light absorption. The static or dc component of the received optical signal represents light absorption by the tissue, venous blood, pigments and other structures. The present invention is concerned with the ac, or pulsatile component because the focus is on examining the wave shape of the systolic portion of the blood volume waveform. Electronically, the dc component is removed with a simple resistor-capacitor high pass circuit that has a −3 dB frequency of around one Hertz.

The amount of light passing through the finger is called transmittance, T, and is defined by:

$$T = I/Io$$

where Io is the intensity of the incident light and I is the intensity of the transmitted light.

The amount of light of a specified wavelength absorbed by a substance is directly proportional to both the length of the light path and the concentration of the material within the light path. The absorbance, A, is defined as the negative logarithm of the transmittance, or:

$$A = -\log T = -\log I/Io = aCL$$

where a is a constant called the extinction coefficient and is dependent on the wavelength of the light passing through the substance and on the chemical nature of the substance. C is the concentration of the substance and L is the path length of the absorbing material.

The present invention makes use of just one of the wavelengths from the pulse oximeter probe, since the objective is to observe only relative changes in the pulse wave shape, which in turn is derived from systolic blood volume changes in the finger. Since a pulse oximeter probe is part of all portable sleep diagnostic screening devices, it is a further object of the present invention to tap into the received light intensity signal of an existing probe, thereby alleviating the need for any additional patient sensors.

Figure 3:
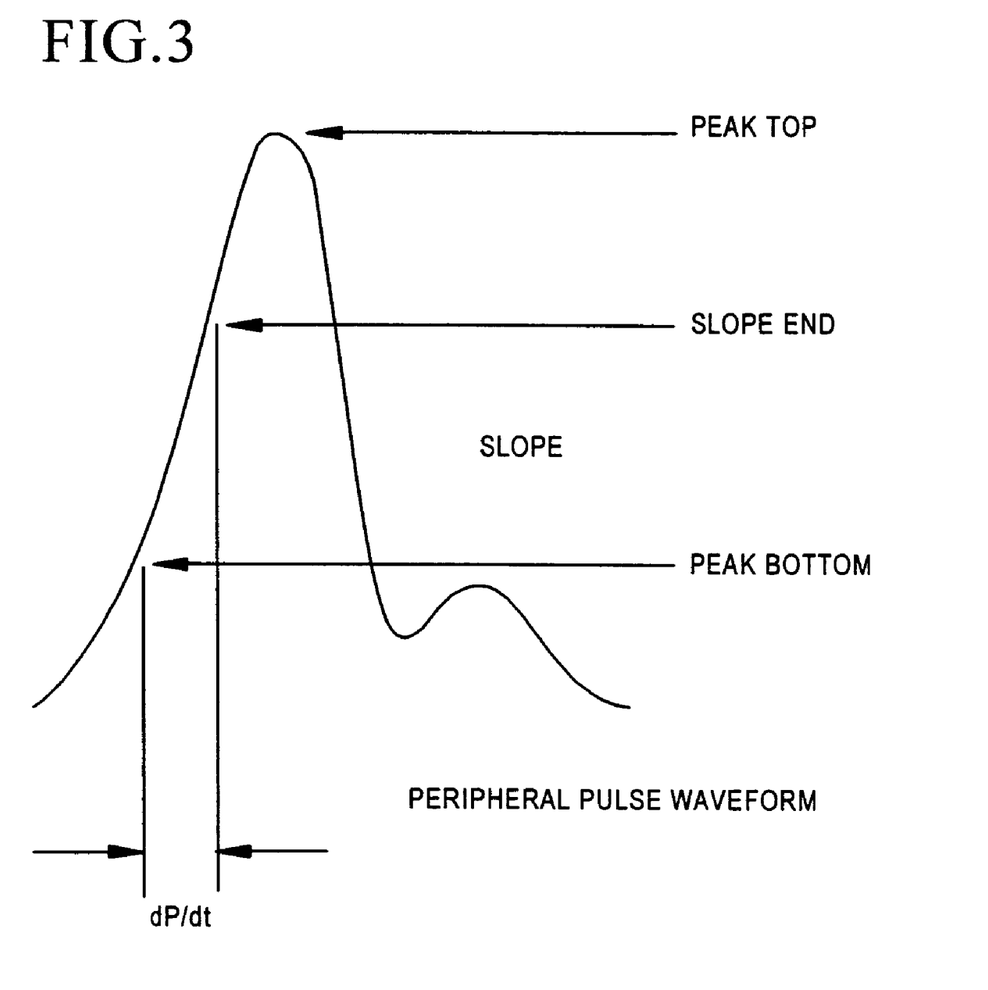
FIG. 3 shows a graphic representation of a single peripheral pulse waveform plotted as volume versus time.

FIG. 3 shows a typical peripheral pulse waveform. Pulse height is the number of A/D counts between the minimum and maximum excursions of each pulse, while the slope is also calculated in A/D counts for a fixed period of time beginning about 40 ms after a minimum is detected.

The first and second derivative waveforms of the photoplethysmographic waveform have characteristic contours, and the contour of the second derivative facilitates the interpretation of the original waves. The analysis of the second derivative of a fingertip photoplethysmogram waveform has been shown to be a good indicator of the effects of vasoconstriction and vasodilation by vasoactive agents, as well as an index of left ventricular afterload as shown in FIGS. 4A, 4B and 4C.

Figure 4A:
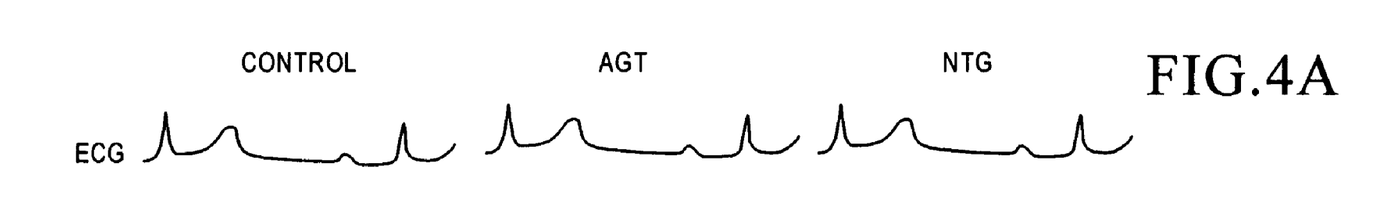
FIG. 4 shows comparative physiological waveforms following administration of vasoactive agents.
Figure 4B:
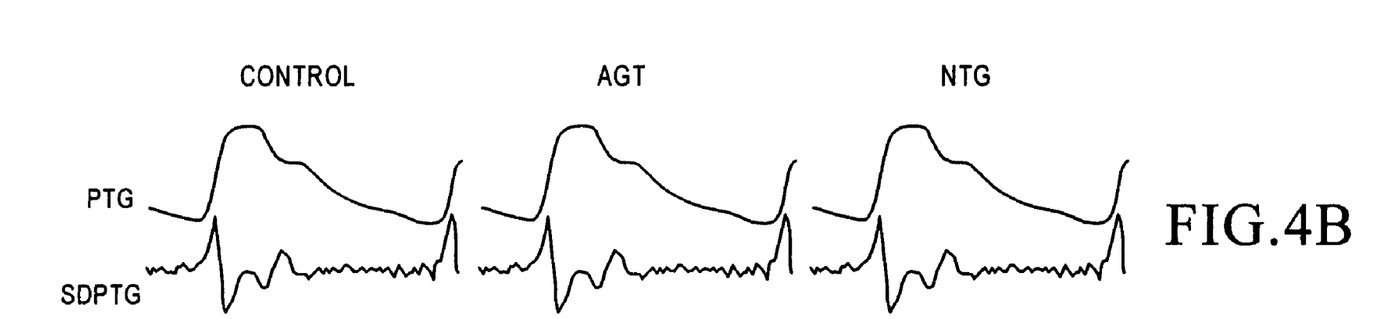
Figure 4C:
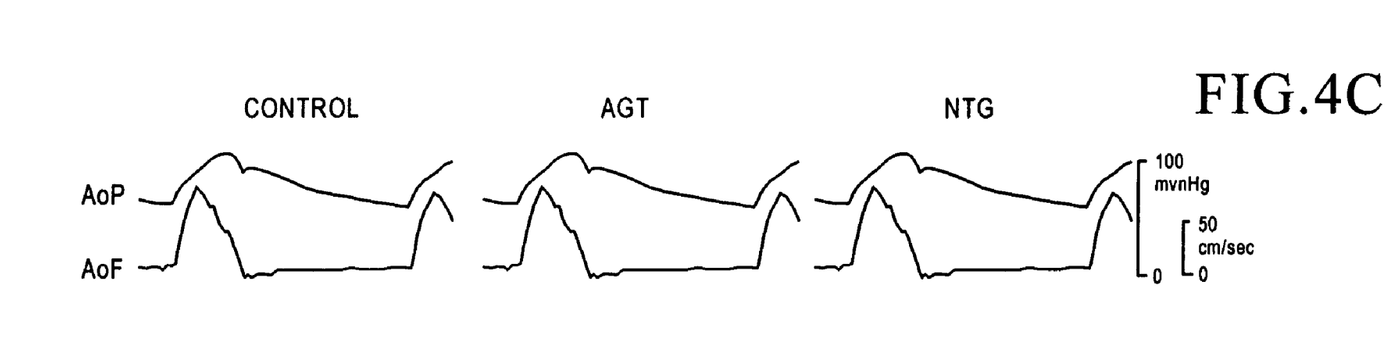

FIGS. 4A, 4B and 4C show waveform tracings demonstrating the results of administration of vasoactive agents. FIG. 4A shows the ECG parameter, FIG. 4B shows corresponding PTG and SDPTG waveforms, and FIG. 4C shows corresponding AoP and AoF waveforms. An increase in the late systolic component of aortic pressure (AoP) and PTG after intravenous injection of 2.5 mg AGT and a deepened d-wave in relation to the height of the a-wave (decreased d/s) are seen in SDPTG. On the other hand, NTG produces marked reduction in late systolic components of aortic pressure and PTG, with d-waves becoming shallower in relation to the height of a wave (increased d/a). AoF indicates ascending aortic flow velocity. Augmentation index (AI) is defined as the ratio of the height of the late systolic peak to that of the early systolic peak, two components of the ascending aortic pressure at the anacrotic notch.

Selected Abbreviations and Acronyms

AGT=Angiotensin

AI=Augmentation Index

NTG=Nitroglycerin

PTG=Photoplethysmography

Figure 5:
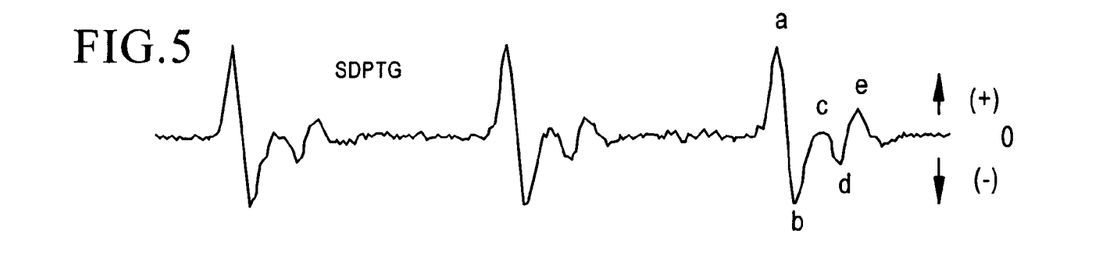
FIG. 5 shows a second derivative waveform consisting of a, b, c and d waves in systole, and an e wave in diastole.

SDPTG=Second Derivative Wave of Fingertip Photoplethysmography, where the a through d components of the second derivative wave are described in FIG. 5. The second derivative waveform consists of a, b, c, and d waves in systole and an e-wave in diastole.

Pulse transitional slope (PTS) technology as applied in the present invention expands on this concept of using photoplethysmographically derived waveforms to assess changes in vascular tension, whether caused by apnaeic obstruction or the more subtle microarousals that are not detectable by cortical means. A normalized slope is calculated by dividing the height achieved during 40 ms of rise time by the maximum height of the pulse waveform (=height of late systolic peak). A normalized slope can be calculated in real time by a microprocessor controlled device as opposed to the post processing (analysis after recording) required by second derivative methods. This will allow use of the present invention technology in labs performing overnight polysomnograph studies in addition to the intended use for home sleep screening.

Since vasoactive drugs have a distinct and predictable affect on the AI when measured by photoplethysmographic methods, by extension the body's own hormonal control of the arterial system shows comparable changes in the pulse waveform when measured using similar techniques.

The present invention provides a portable, simple, and cost effective sleep diagnostic method and apparatus capable of detecting arousals and microarousals without adding EEG electrodes or additional patient sensors beyond those worn during a typical home study.

Since microarousals have been associated with changes in autonomic system outflow, an object of the present invention is to provide a small, portable device that analyzes the shape of the arterial finger pulse, thereby detecting on a beat by beat basis changes in vascular tone directly attributable to microarousals. The present invention uses a photoplethysmographically derived arterial blood volume waveform for monitoring change in peripheral arterial vascular tone in conjunction with A/D converters and a microcontroller for analyzing the morphology of the pulsatile signal.

Detection of microarousals by the present invention compares favorably with results achieved using pulse transit time (PTT) devices, EEG analysis, ECG analysis, esophagal pressure (Pes), and combinations of these methods. Although PTT and peripheral arterial tonometry (PAT) have both been receiving much attention as techniques for detecting changes in the ANS during sleep studies, PAT is relatively expensive and PTT has implementation problems caused by motion artifact.

Efficacy of the present invention has been verified through monitoring of test subjects performing a "Valsalva Maneuver," which is the quickest and most dramatic method of producing ANS discharge—a resulting increase in intrapulmonic pressure produced by forcible exhalation against the closed glottis. This produces a sympathetic discharge with subsequent vascular constriction.

Figure 6:
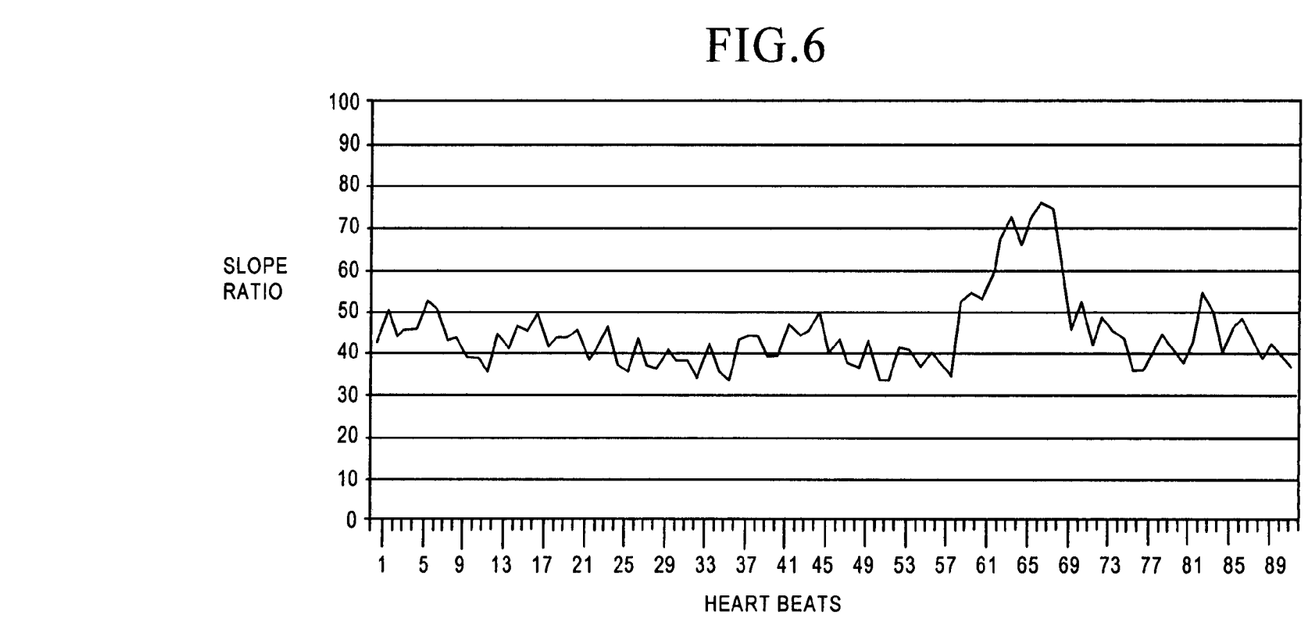
FIG. 6 shows a graphic representation of changes in Normalized Slope plotted as slope ratio versus heart beats while subject performs Valsalva maneuver.

A typical response to the Valsalva Maneuver is shown in FIG. 6. The normalized slope increases significantly, around 30% on the average which we postulate to be caused by increased rate of heart tissue conduction, increased contraction force, and increased rigidity in the arterioles. FIG. 6 shows changes in Normalized Slope produced by the present invention during a Valsalva Maneuver. The increase in ANS outflow begins around heart beat 59, indicated by the sharp rise in the normalized slope of he pulsatile arteriole waveform.

Further testing was conducted using daytime nap studies—Several short daytime nap studies were performed on sleep deprived volunteers for the purpose of scoring the sleep stages during these naps and looking for correlations between the stages and recorded normalized PTS slopes. None of the subjects were known to have sleep disordered breathing. Volunteers were monitored with two central lobe electroencephalographic EEG electrodes, two occipital EEG electrodes, two electrooculogram (EOG) electrodes, a chin electrode, a nasal air flow device, two respiratory airflow belts, and a PTS apparatus of the present invention, which provided a normalized slope value on a beat to beat basis.

Figure 7A:
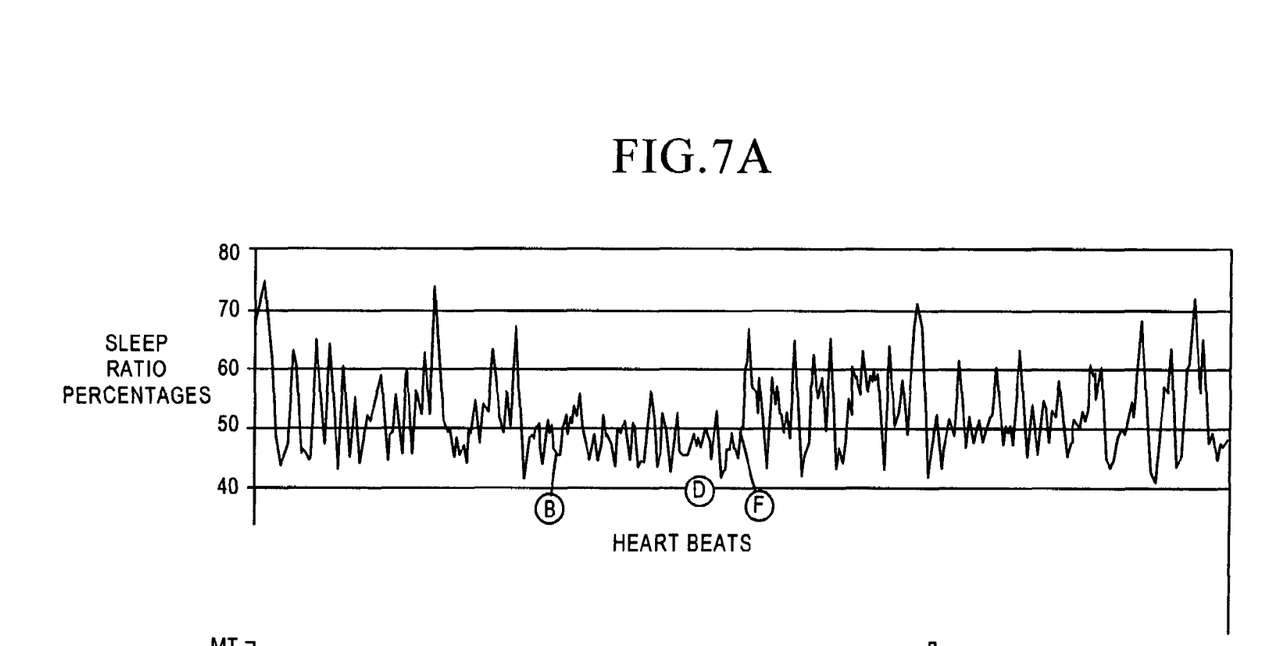
FIG. 7 shows a sleep stage hypnogram of an hour and a quarter sleep study.
Figure 7B:
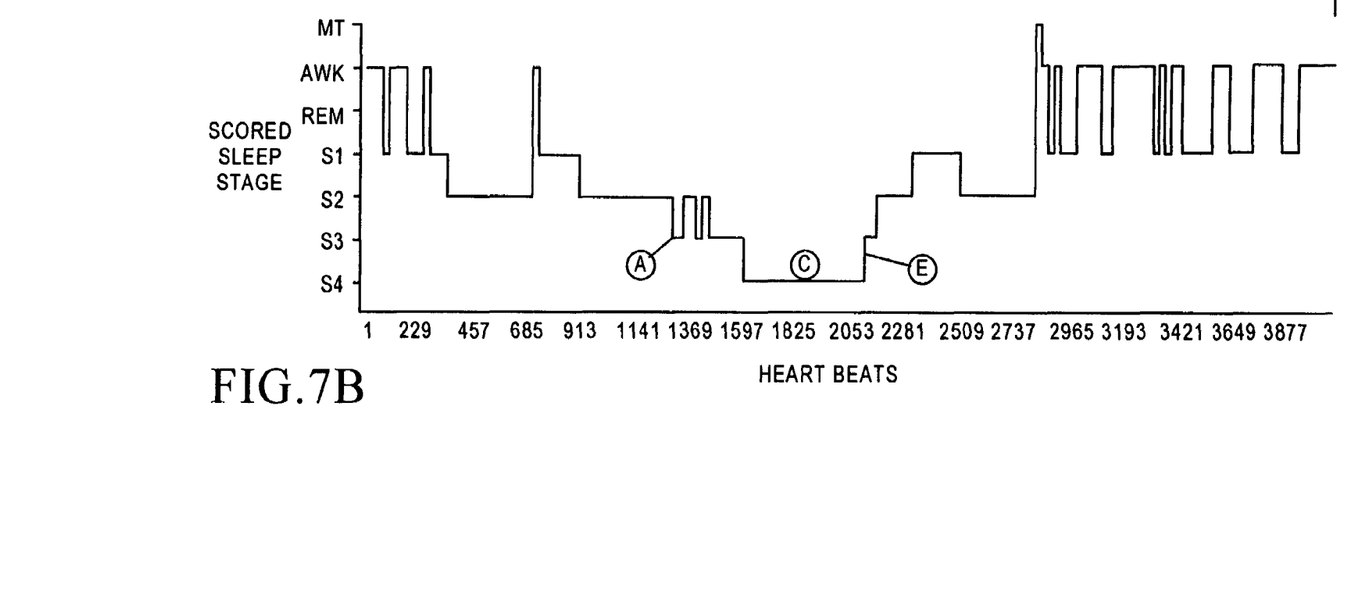

A typical recording of the normalized slope (on a scale of 0 to 100, where 100 is vertical) versus the sleep stages is shown in FIGS. 7A and 7B. The sleep stages were scored by a registered polysomnographic technologist (RPSGT) from the EEG, EOG, and respiratory waveforms. FIGS. 7A and 7B show a sleep stage hypnogram of an hour and a quarter sleep study. FIG. 7A shows sleep ratio percentages through the duration of the study. FIG. 7B shows a graph that has been scored from EEG, EOG, and respiratory waveforms according to the sleep scoring convention of the American Sleep Academy. Point A is the beginning of stage 3 sleep, corresponding to point B on the normalized pulse slope diagram. Area C is stage 4, and a definitive corresponding area of reduced slope values can be seen in the area labeled D. As sleep becomes lighter, rising from at point E to stage 3 and then stage 2, a corresponding rise in slope can be seen starting at point F.

Figure 8:
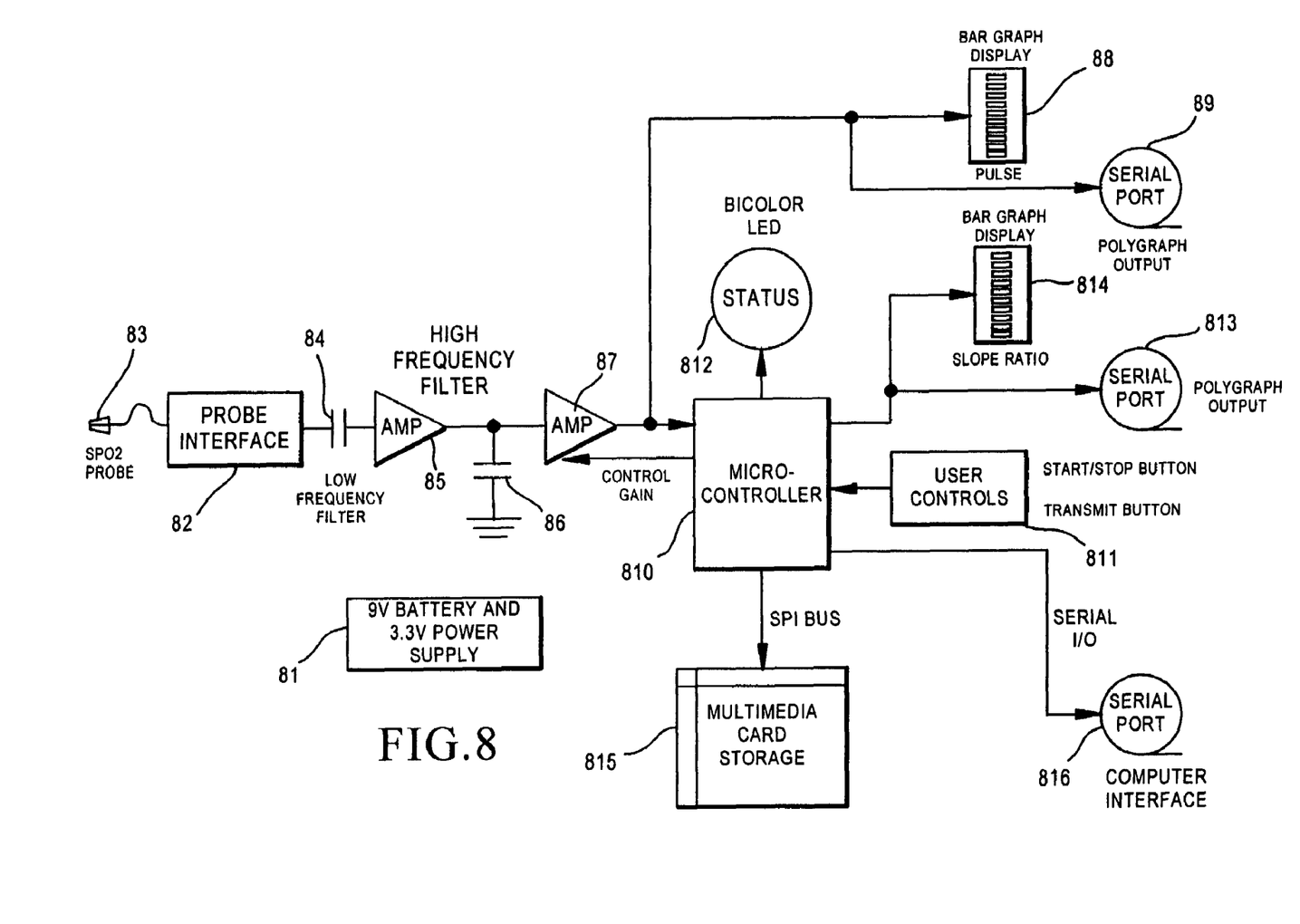
FIG. 8 shows a block diagram of the present invention apparatus.

A block diagram of a preferred embodiment of the present invention apparatus is shown in FIG. 8. The device is battery powered 81, with sufficient capacity for a 12 hour overnight study; analog circuitry for voltage regulation and power supply conditioning; the device has an interface 82 for an OEM supplied finger pulse oximetry probe 83; a low frequency front-end filter 84 for probe input signals; an input signal pre-amplifier 85; a high frequency filter 86; a gain-controlled signal amplifier stage 87; a bar graph display for indication of a pulse signal 88; a polygraph output 89 for pulse signal data; a means of digital processing via a microprocessor or microcontroller 810 to provide slope detection and peak to peak height determination of each systolic finger pulse, mathematical normalization of the slope, digital to analog (D/A) conversion of the slope value for polysomnographic display, and digital control of the finger probe gain, and having a status indicator LED 812; user controls 811 including start/stop and transmit functions; a polygraph output 813 for slope ratio data; a bar graph display 814 for visual indication of slope ratio information; means to permit 12 hours (minimum) of data storage, such as on-board multi-media card storage 815; and analog and/or digital outputs 816 for providing output of the pulsatile waveform and a DC level representative of the normalized slope, and slope ratio data.

The present invention provides a constant excitation to the pulse oximeter finger probe LED to evaluate the overall concept of slope detection without actually using the OEM's pulse oximeter circuit board. In an alternative embodiment, a pulse oximeter printed circuit board (PCB) is incorporated as a daughter board (internal to the device).

Normalization is a method to correct for the photoplethysmographic pulse signal morphological changes based on finger position (as opposed to actual changes of autonomic activity.) Currently used ANS activity monitoring methods such as PTT and PAT lack the capability for normalization of incoming data and therefor cannot correct for finger position changes. The present invention includes a process for normalization, and thus provides immunity to artifact caused by both elevation changes of the finger probe, and changes in blood flow due to arterial compression during patient positional changes.

The obtained photoplethysmographic signal can be normalized to minimize changes in peak to peak signal amplitude that are not due to ANS activity. In other words, if there is a vertical peak to peak percentage increase of the pulsatile waveform (and consequent increase in slope), but otherwise no waveform distortion, the percentage increase is likely to have been caused by a changing of position (relative to the heart) of the finger probe. If this same increase in peak to peak height occurred, but there was also a slight shift in the waveform shape, becoming slightly more of a square wave from its sinusoidal shape, then the increased slope is likely to be the effect of ANS activity, such as increased heart contractility.

The present invention normalizes the slope of each blood pressure pulse by dividing the slope by the peak to peak height of that same pulse. For each pulsatile beat with a constant period and shape over a relatively short period of time, the normalization will remove variations due to height only. Both the height and peak will actually be measured in terms of analog-to-digital (A/D) counts in the PTS unit's microcontroller. Research on finger vascular tone has shown that normalized pulse volume, also derived photoplethysmographically, appears to be superior to the conventional pulse volume.

The present invention is intended to make use of an existing single photoplethysmmographic (optical volume detecting) probe, and therefore existing pulse oximetry technology. Since pulse oximeters use an alternating flashing of two different wavelength LEDs, the present invention synchronizes with the desired LED in order to examine the transmitted intensity due to a single wavelength. Alternatively, certain models of oximeter OEM modules provide an analog or digital output that can be utilized directly by the present device.

In a preferred embodiment, the apparatus contains an autogain circuit to prevent the pulsatile waveform from clipping during changes in finger height, large blood pressure changes, and between patients with different thickness and skin color fingers. There are also several peak detection algorithms for detecting the beginning of the systolic rise time and the beginning of diastole. These algorithms provide the minimal quantizing noise, something that can occur when attempting to lock onto the rounded peak of a waveform. With sufficiently fast sampling and the correct threshold for detecting a zero slope (peak) the circuit was designed to not trigger on noise and yet be sensitive enough to be very close to the peak and not loose accuracy due to detection well beyond the peak.

Alternative embodiments of the present invention provide algorithms for slope detection, peak to peak height, and normalization in the form of firmware within the device, or by software after the data is downloaded into the polysomnograph. Alternative methods of data storage and transfer are also possible, including multimedia card storage, computer hard drive storage, serial input/output interface with other devices, and various forms of telemetry and phone transmission. Various embodiments for displaying pulse rate and slope ratio can include waveform displays, light bars, and numerical information.

Figure 9:
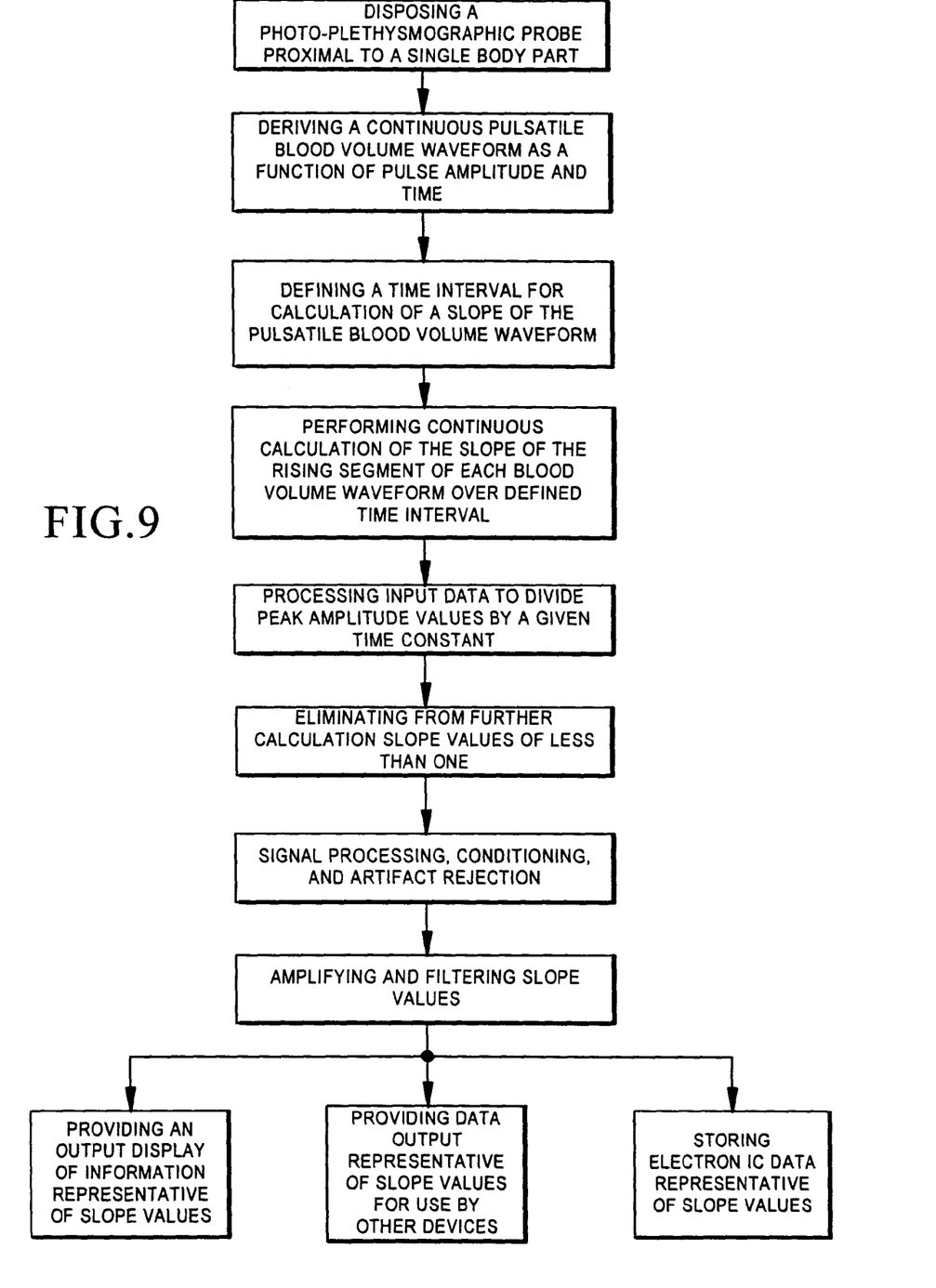
FIG. 9 shows a block diagram of the present invention method.

FIG. 9 shows a block diagram of the method of the present invention. Shown are the steps of disposing a photoplethysmographic probe proximal to a single body part; deriving a continuous pulsatile blood pressure waveform as a function of amplitude and time; defining a time interval for calculation of a slope of the pulsatile blood pressure waveform; performing continuous calculation of the slope of each blood pressure waveform over a defined time interval; processing input data to divide peak amplitude values by a given time constant; eliminating from further calculation slope values of less than one; signal processing, conditioning, and artifact rejection; amplifying and filtering normalized slope values; and providing output information representative of pulse and slope ratio in the form of a display, electronic data output, and data storage.

INDUSTRIAL APPLICABILITY

The present invention has applicability to the field of medical devices, and more particularly to a physiological monitoring method and device used for detection of autonomic nervous system (ANS) activity in the field of sleep research.

In compliance with the statute, the invention has been described in language more or less specific as to sleep diagnostic medical devices. It is to be understood, however, that the invention is not limited to the specific means or features shown or described, since the means and features shown or described comprise preferred ways of putting the invention into effect.

Additionally, while this invention is described in terms of being used for sleep diagnostic studies, it will be readily apparent to those skilled in the art that the invention can be adapted to other uses for other forms of medical and non-medical monitoring of the autonomic nervous system as well, and therefore the invention should not be construed as being limited to sleep study applications. The invention is, therefore, claimed in any of its forms or modifications within the legitimate and valid scope of the appended claims, appropriately interpreted in accordance with the doctrine of equivalents.

We claim:

1. An apparatus for monitoring human autonomic nervous system activity using pulsatile blood volume waveform signals, said apparatus comprising:
   a photoplethysmographic probe having a light emitting element and an opposing light detecting element, and having an output signal indicating changes in blood volume on at least one alpha andrenergic receptor site of a human body;
   a processor element, responsive to said output signal indicating changes in blood volume, said processor element defining a time interval for calculation of slope of blood volume waveform continuously and in real time and reducing said waveform signals to a slope value within said time interval;
   said processor element containing an algorithm for normalization of the slope value;
   said processor element containing an artifact rejection algorithm for eliminating from further processing slope values less than one; and
   amplifier and filter circuitry for rendering output signals representative of said slope values.

2. The apparatus of claim 1, wherein the photoplethysmographic probe is adapted for application on a finger.

3. The apparatus of claim 1, wherein the photoplethysmographic probe is adapted for indirect application to the alpha andrenergic receptor site, whereby no direct contact with a body part is required.

4. The apparatus of claim 3, further comprising a display for indicating information representative of pulsatile blood volume waveform signals.

5. The apparatus of claim 3, further comprising a display for indicating information representative of slope values.

6. The apparatus of claim 3, further comprising a display for indicating information representative of a slope ratio.

7. The apparatus of claim 1, further comprising at display for visual indication of output signals.

8. The apparatus of claim 1, further comprising an electronic storage medium for data storage capability.

9. The apparatus of claim 1, further comprising at least one data part for downloading output signals.

10. A method for identification of human autonomic nervous system activity, the method comprising the steps of:
    disposing a photoplethysmographic probe proximate to a single alpha andrenergic receptor site of a human body part;
    obtaining an electrical signal from said probe representative of pulsatile blood volume within said body part;
    deriving a pulsatile blood volume waveform as a function of amplitude and time;
    defining a time interval for calculation of a slope of the pulsatile blood volume waveform;
    applying an algorithm that continuously provides real-time calculation of the slope along said waveform within said time interval;
    dividing peak amplitude values by a time constant and eliminating slope values less than 1, whereby artifact elimination is achieved;
    normalizing slope values; and providing information representative of slope values, whereby autonomie nervous system activity is monitored.

11. The method of claim 10 further comprising the step of applying signal filtration means, wherein undesirable low and high frequency signal components are eliminated.

12. The method of claim 10 further comprising the step of monitoring the pulsatile blood volume amplitude.

13. The method of claim 10 further comprising the step of amplifying and filtering slope values, whereby improved sensitivity and accuracy is achieved.

14. The method of claim 10 further comprising the step of providing an output display of visual information representative of slope values.

15. The method of claim 10 further comprising the step of providing data output representative of input data and slope values.

16. The method of claim 10 further comprising the step of providing a means for storing data representative of input data and slope values.

* * * * *